(12) United States Patent
Van De Haar

(10) Patent No.: US 7,657,001 B2
(45) Date of Patent: Feb. 2, 2010

(54) METHOD FOR REDUCING 3D GHOST ARTEFACTS IN AN X-RAY DETECTOR

(75) Inventor: Peter George Van De Haar, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/093,043

(22) PCT Filed: Nov. 7, 2006

(86) PCT No.: PCT/IB2006/054148

§ 371 (c)(1),
(2), (4) Date: May 8, 2008

(87) PCT Pub. No.: WO2007/054893

PCT Pub. Date: May 18, 2007

(65) Prior Publication Data

US 2009/0060138 A1  Mar. 5, 2009

(30) Foreign Application Priority Data

Nov. 9, 2005  (EP) .................. 05110553

(51) Int. Cl.
*H05G 1/54* (2006.01)
*H05G 1/56* (2006.01)
*H05G 1/64* (2006.01)

(52) U.S. Cl. .................. 378/116; 378/114; 378/98.8
(58) Field of Classification Search .................. 378/4, 378/19, 98.8–98.12, 165, 207, 116, 114
See application file for complete search history.

(56) References Cited

U.S. PATENT DOCUMENTS

| 5,920,070 | A | * | 7/1999 | Petrick et al. ......... 250/370.09 |
| 5,923,722 | A | * | 7/1999 | Schulz ................... 378/98.8 |
| 6,256,404 | B1 | | 7/2001 | Gordon et al. |
| 6,353,654 | B1 | * | 3/2002 | Granfors et al. .......... 378/62 |
| 6,744,912 | B2 | * | 6/2004 | Colbeth et al. ........... 382/132 |
| 2005/0058251 | A1 | | 3/2005 | Spahn |
| 2005/0092909 | A1 | | 5/2005 | Spahn |
| 2005/0151086 | A1 | | 7/2005 | Spahn |

FOREIGN PATENT DOCUMENTS

| DE | 10331522 A1 | 2/2005 |
| WO | WO03100460 A1 | 12/2003 |

OTHER PUBLICATIONS

Siewerdsen et al: "A Ghost Story: Spatio-Temporal Response Characteristics of an Indirect-Detection Flat-Panel Imager"; Medical Physics, vol. 26, No. 8, August 1999, pp. 1624-1641.

Roberts et al: "Charge Trapping At High Doses in an Active Matrix Flat Panel Dosimeter"; IEEE Transactions on Nuclear Science, vol. 51, No. 4, Aug. 2004, pp. 1427-1433.

(Continued)

*Primary Examiner*—Irakli Kiknadze

(57) ABSTRACT

A method for at least reducing the occurrence of differential ghosting in an X-ray image acquired in respect of a subject, wherein a deghost scan is performed at least once daily so as to generate an underlying strong homogeneous ghost so that further differential (non-homogeneous) ghosting during subsequent scans is minimised. The deghost scan comprises acquiring an 'air' image, when no subject is present between the X-ray source (4) and detector (5), as a relatively high detector dose.

8 Claims, 4 Drawing Sheets

OTHER PUBLICATIONS

Overdick et al: "Temporal Artefacts in Flat Dynamic X-Ray Detectors"; Medical Imaging 2001: Physics of Medical Imaging, Proceedings of SPIE, vol. 4320, 2001, pp. 47-58.

Jing et al: "Amorphous Silicon Pixel Layers With Cesium Iodide Converters for Medical Radiography"; IEEE Transactions on Nuclear Science, vol. 41, No. 4, August 1994, pp. 903-909.

* cited by examiner

METHOD FOR REDUCING 3D GHOST ARTEFACTS IN AN X-RAY DETECTOR

The invention relates to a method for reducing 3D ghost artefacts in an X-ray detector, particularly suitable, but not necessarily exclusively for use during soft tissue imaging with, for example, C-arm and Volume CT (computer tomography) systems.

Referring to FIG. 1 of the drawings, a typical X-ray system comprises a swing arm (C-arc or G-arc) 1 supported proximal a patient table 2 by a robotic arm 3. Housed within the swing arm 1, there is provided an X-ray tube 4 and an X-ray detector 5 being arranged and configured to receive X-rays which have passed through a patient (not shown) and generate an electrical signal representative of the intensity distribution thereof, from which a 3D image of the irradiated zone of the patient can be reconstructed. By moving the swing arm 1, the X-ray tube 4 and detector 5 can be placed at any desired location and orientation relative to a patient lying on the patient table 2. The 3D reconstructed image of the irradiated zone of the patient is displayed on a display screen 6.

The X-ray detector 5 is typically a flat detector (FD) which comprises a conversion layer containing Caesium-iodide doped with Thallium (CsI:Tl) for converting X-radiation into optical radiation, and a plurality of photosensitive elements to derive electronic signals from the optical radiation. Such an X-ray detector is known from the paper '*Amorphous silicon pixel layers with Caesium Iodide converter for medical radiography*', by T. Jing et al. in IEEE Transactions in nuclear science 41(1994)903-909. The convertor layer of the known X-ray detector is formed as a CsI:Tl layer with a thickness in the range from 65 to 220 μm. Amorphous silicon pin-diodes are used as the photosensitive elements which detect scintillation light produced by X-radiation incident on the CsI:Tl layer. The Tl-doping level is kept at 0.1-0.2 mol %.

Although the conversion layer of the known X-ray detector has a high conversion efficiency, it suffers from substantial afterglow. Afterglow is the phenomenon, that upon incidence of X-rays, the optical radiation generated in the conversion layer continues for some (short) time after the incidence of X-rays has ceased, caused by a so-called "trapping" effect in the conversion layer or scintillator. International Patent Application No. WO 03/100460 describes an X-ray detector with a CsI:Tl conversion layer in which the CsI:Tl is ultrapure and the Tl-doping level is in the range of 0.25-1.00 at %. As a result, the level of optical radiation continuing to be generated after the incidence of X-rays is reduced and afterglow is therefore reduced accordingly.

Brightburn or "ghosting" is another (more long term) phenomenon caused by "trapping" that is caused by gain effects in the scintillator, and which causes long-lasting ghosts which typically create circular artefacts in the displayed image, and to which 3D reconstruction is very susceptible.

It is an object of the present invention to provide an improved method of further reducing the appearance in a 3D reconstructed image of artefacts caused by ghosting in an X-ray detector.

In accordance with the present invention, there is provided a method for reducing differential ghosting in an X-ray image acquired in respect of a subject using an X-ray system comprising an X-ray source for irradiating said subject and an X-ray detector for receiving X-radiation that has passed through said subject and generating an electric signal representative of the intensity distribution thereof, said X-ray detector comprising a scintillator for receiving X-radiation incident thereon and converting said X-radiation into optical radiation, the method comprising periodically acquiring a deghost scan when no subject is present between said X-ray source and X-ray detector by causing said X-ray source to generate an X-radiation beam and causing said detector to receive said X-radiation and generate an electric signal representative of homogeneous ghosting caused in said detector by said X-radiation incident thereon.

Thus, the occurrence of differential ghosting in scans acquired subsequent to the acquisition of the deghost scan is substantially reduced because the deghost scan causes a high degree of "trapping" in the scintillator (which is typically a CsI:Tl scintillator) such that no further significant ghosting can be generated during each subsequent scan.

Preferably, the deghost scan is performed at least once daily, possibly automatically when the X-ray system is switched on. The deghost scan is beneficially performed at a relatively high X-radiation detector dose, typically of substantially the same order of that used to acquire subsequent scans in respect of respective subjects.

These and other aspects of the present invention will be apparent from, and elucidated with reference to, the embodiments described herein.

Embodiments of the present invention will now be described by way of examples only and with reference to the accompanying drawings, in which.

Figure 1:
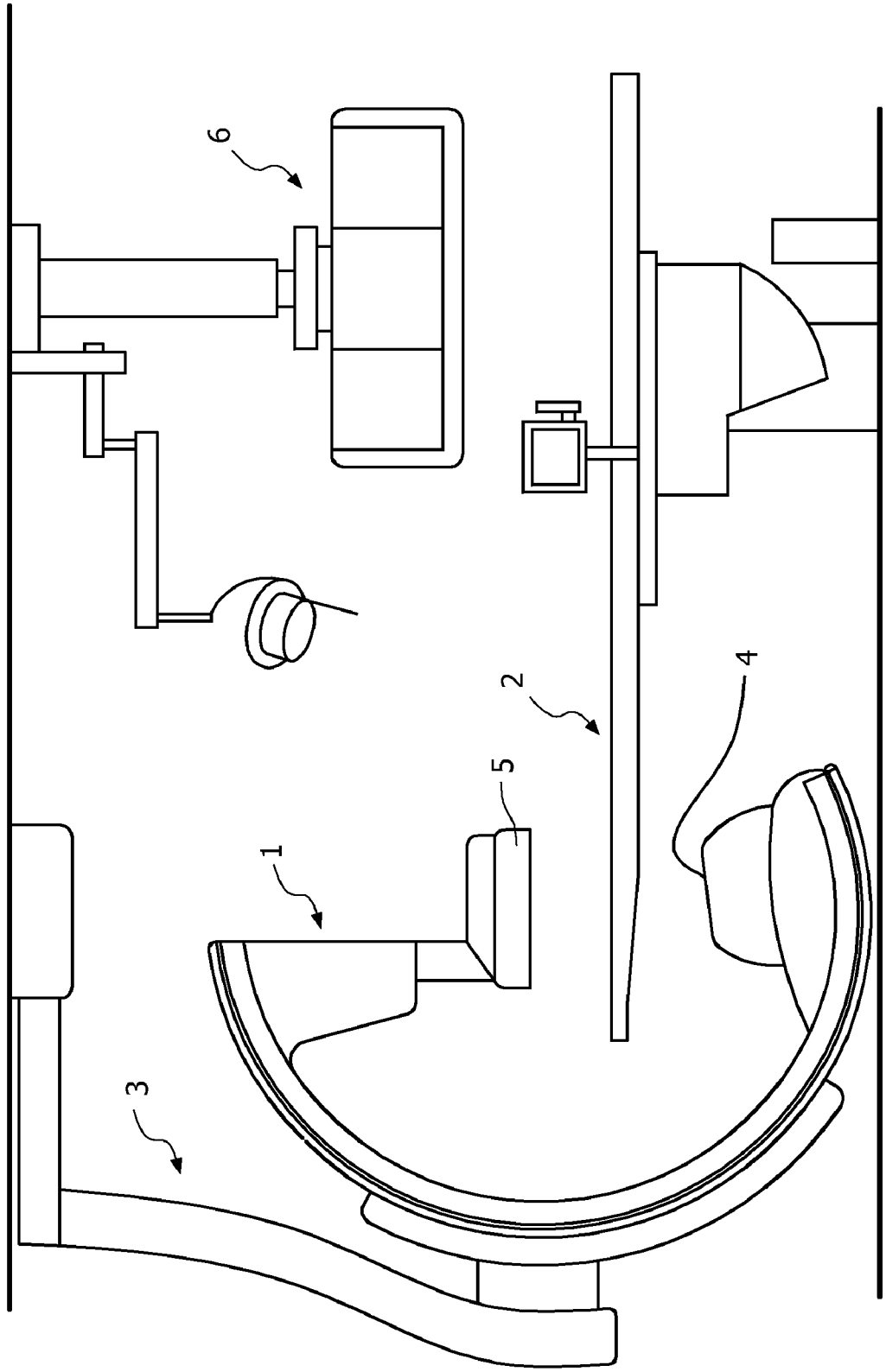
FIG. 1 is a schematic side view of an X-ray system employing an X-ray detector according to an exemplary embodiment of the present invention.
Figure 2:
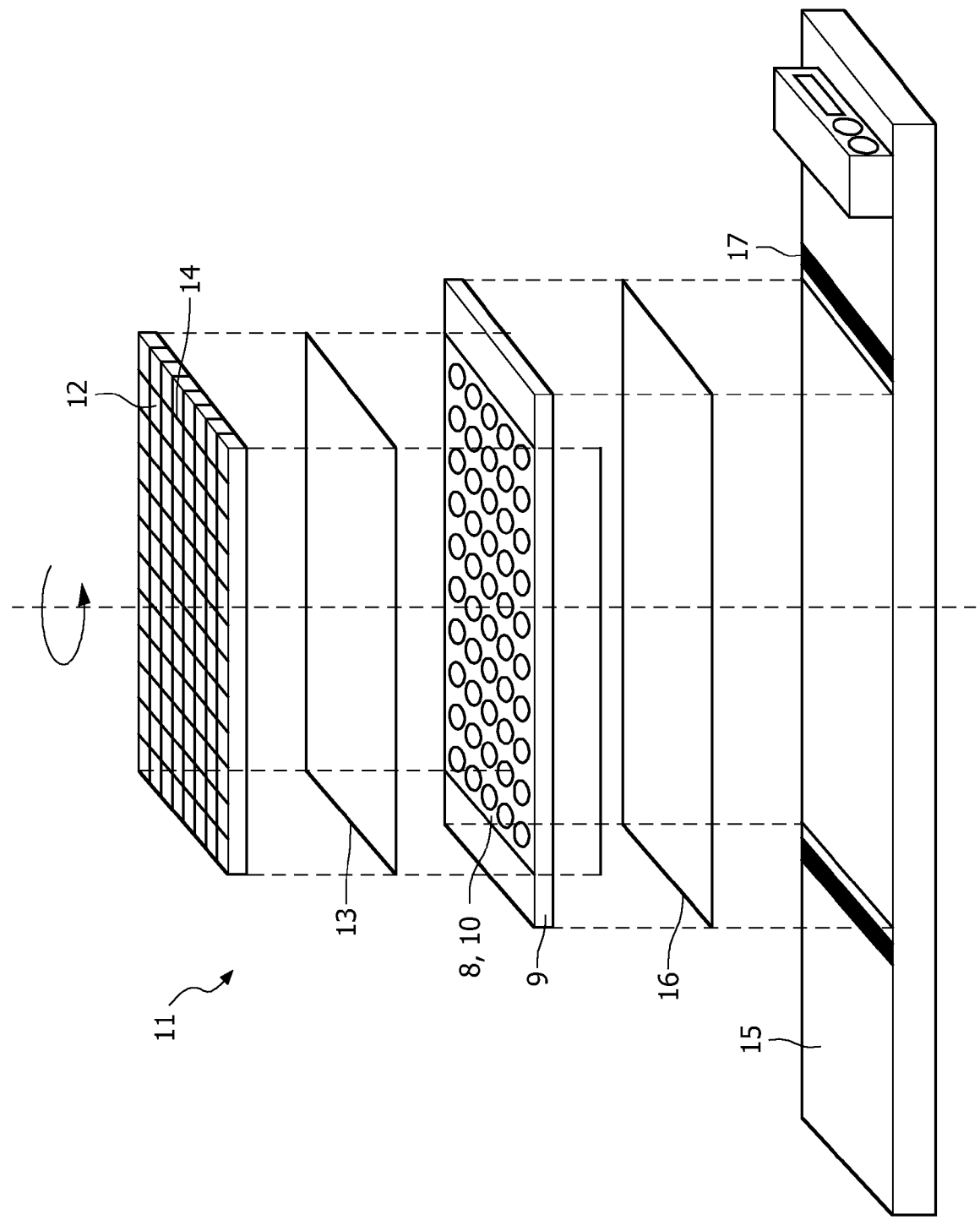
FIG. 2 is an exploded view of a CMOS chip with a plurality of detector elements.

A flat X-ray detector employed in a system such as that described with reference to, and illustrated in, FIG. 1 of the drawings is typically composed of a plurality of detector elements which are arranged in a plurality of rows. FIG. 2 shows an exploded view of a CMS substrate forming such a detector and having a plurality of detector elements. A plurality of photodiodes 8 and the associated amplifier elements (not shown) are realised in an integrated semiconductor technique on the same substrate. Thus, a CMOS chip 9 is realised on which the detector elements 10 (also referred to as picture elements or pixels) are arranged in the form of a matrix; for example, in this case, they are arranged in six rows in the longitudinal direction and in nine columns in the transverse direction. A complete detector array 3 customarily consists of a plurality of consecutively-arranged chips 9.

Over each CMOS chip 9 there is arranged a conversion layer formed by a scintillator 11 which is as large as the CMOS chip 9. The scintillator 11 is formed by Tl-doped CsI and is connected to the CMOS chip so as to be exactly positioned with respect thereto by means of a thin layer of an optical adhesive 13. Absorber layers 14 are provided between the individual crystals 12 of the scintillator.

The CMOS chips 9 are mounted on a printed circuit board or PCB 15 by means of an adhesive layer 16. The electrical connections from the CMOS chip 9 to the PCB 15 are formed by leads to the bond pads 17.

Figure 3:
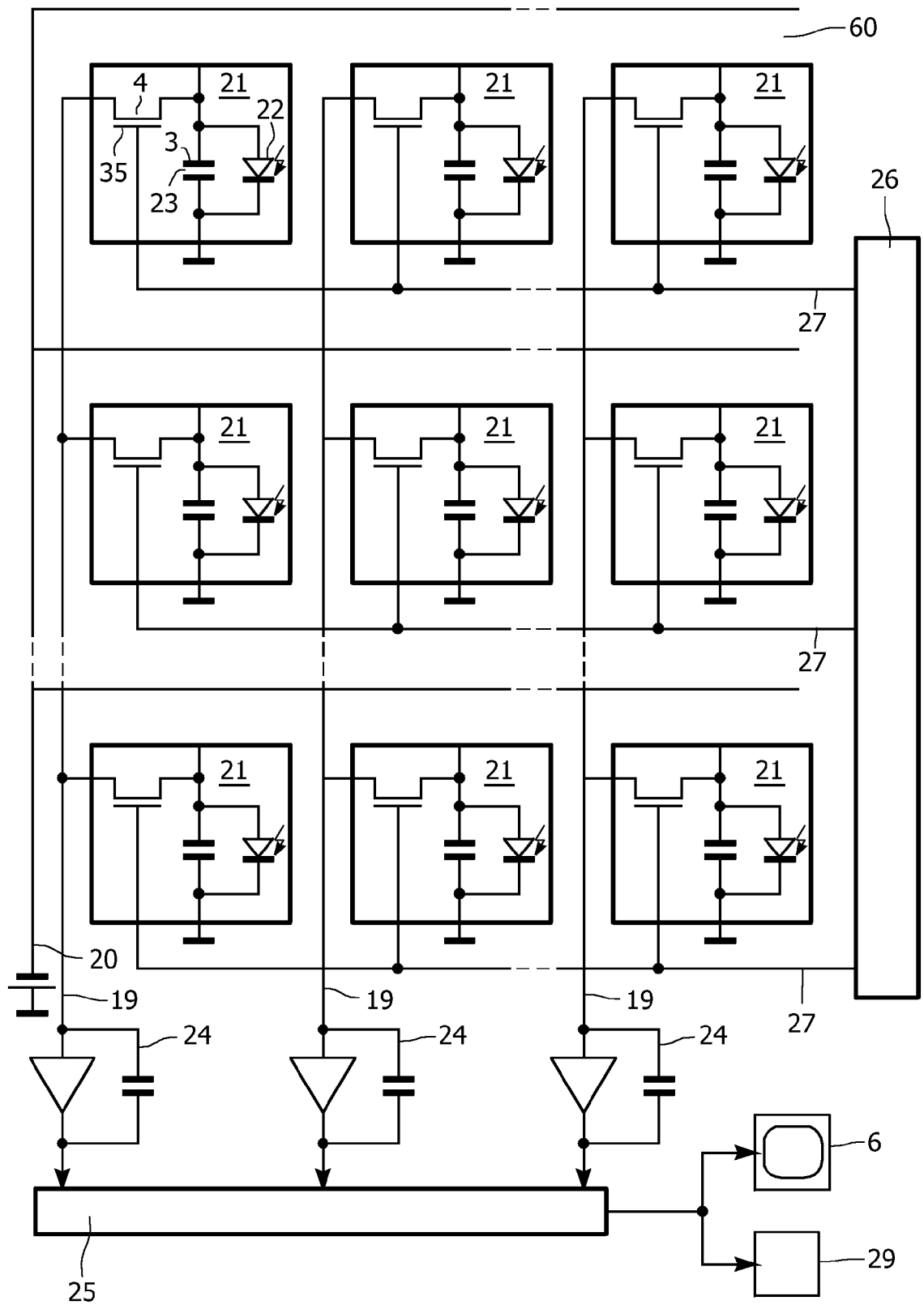
FIG. 3 shows a circuit diagram of a sensor matrix incorporated in an X-ray detector of an exemplary X-ray system.

When X-radiation is incident on the detector, the X-ray quanta (γ) are absorbed in the scinitillator 11 and converted into visible light. Referring to FIG. 3 of the drawings, for each pixel in an X-ray image there is provided a sensor element 21 which comprises a photo-sensor element 22, a collecting capacitance 23 and a switching element 40. Electric charges are derived from incident X-rays by the photo-sensor element 22, which electric charges are collected by the collection capacitance 23. The collecting electrodes 3 form part of respective collecting capacitances 23. For each column of sensor elements there is provided a respective read-line 19 and each collecting capacitance 23 is coupled to its respective read-line 19 by way of its switching element 40. The photosensor elements are provided on a substrate 60, and although as an example, FIG. 3 shows only 3×3 sensor elements, in a practical embodiment, a much larger number of sensor elements, say 2000×2000, is employed.

In order to read-out the collected electric charges, the relevant switching elements 40 are closed so as to pass electric charges from the collecting capacitances down respective read-lines. Separate read-lines 19 are coupled to respective highly sensitive output amplifiers 24 of which the output signals are supplied to a multiplex circuit 25. The electronic image signal is composed from the output signals by the multiplex circuit 25. The switching elements 40 are controlled by means of a row-driver circuit 26 which is coupled to the switching elements for each row by means of addressing lines 27. The multiplex circuit supplies the electronic image signal to, for example, a monitor 6 on which the image information of the X-ray image is then displayed or the electronic image signal may be supplied to an image processor 29 for further processing.

Thus, referring back to FIG. 1 of the drawings, in a known X-ray system, a patient to be examined is positioned on the patient table 2 and is then irradiated with an X-ray beam which is emitted by the X-ray tube 4. Owing to local differences of the X-ray absorption in the patient, an X-ray shadow image is formed on the X-ray detector. By the sensor matrix which is incorporated in the X-ray detector 5, the X-ray image is converted into an electronic image signal. The electronic image signal is supplied to the monitor 6 on which the image information of the X-ray image is displayed.

As explained above, the CsI:Tl scintillator used in the flat detector suffers from the drawback that long-lasting ghosts occur, which have an adverse effect on the quality of the 3D reconstructed image in that they (typically) cause circular artefacts to appear therein. Such ghost images are caused by differential gain effects in the scintillator, generated through non-homogeneous radiation in combination with trapping effects in the scintillator. Since ghosting is a gain effect, it can (theoretically) be corrected through applying gain correction. Gain correction is based on 'air' images (i.e. images acquired without any object between the X-ray tube and the X-ray detector (and without collimation), and the ghost is "divided out" of the object images when gain correction is applied. However, if the gain scan is performed (i.e. the air image is acquired) before the afterglow is generated in the scintillator, then such gain correction will fail. In other words, ghosting tends to change with each scan, whereas a gain scan (in a conventional method) can only be acquired once daily, and the gain correction method described above is therefore unable to cope with changing ghosts.

This problem is overcome, in accordance with an exemplary embodiment of the present invention, by acquiring (preferably at the start of each day) a "deghost" scan ('air' scan) with a very high (accumulated) detector dose (ca. 40 mGy). This results in a strong, but homogeneous, ghost 9 because most of the scintillator traps are filled), thereby preventing further generation of strong differential ghosts. Thus, an underlying strong ghost is generated in the first instance, so that the same underlying ghosting is present in all subsequently-acquired scans, and no further differential (changing) ghosts are generated that need to be corrected for. Thus, non-homogenous ghosting is suppressed by the generation of a strong but homogeneous ghost during an initial "deghost" scan. Ghosting typically decays on a time scale of around a day, so the deghost scan should preferably be repeated once per day. A system which has not been used for a few days is therefore very susceptibe to differential ghosting unless the "deghost" scan has been performed initially.

Figure 4:
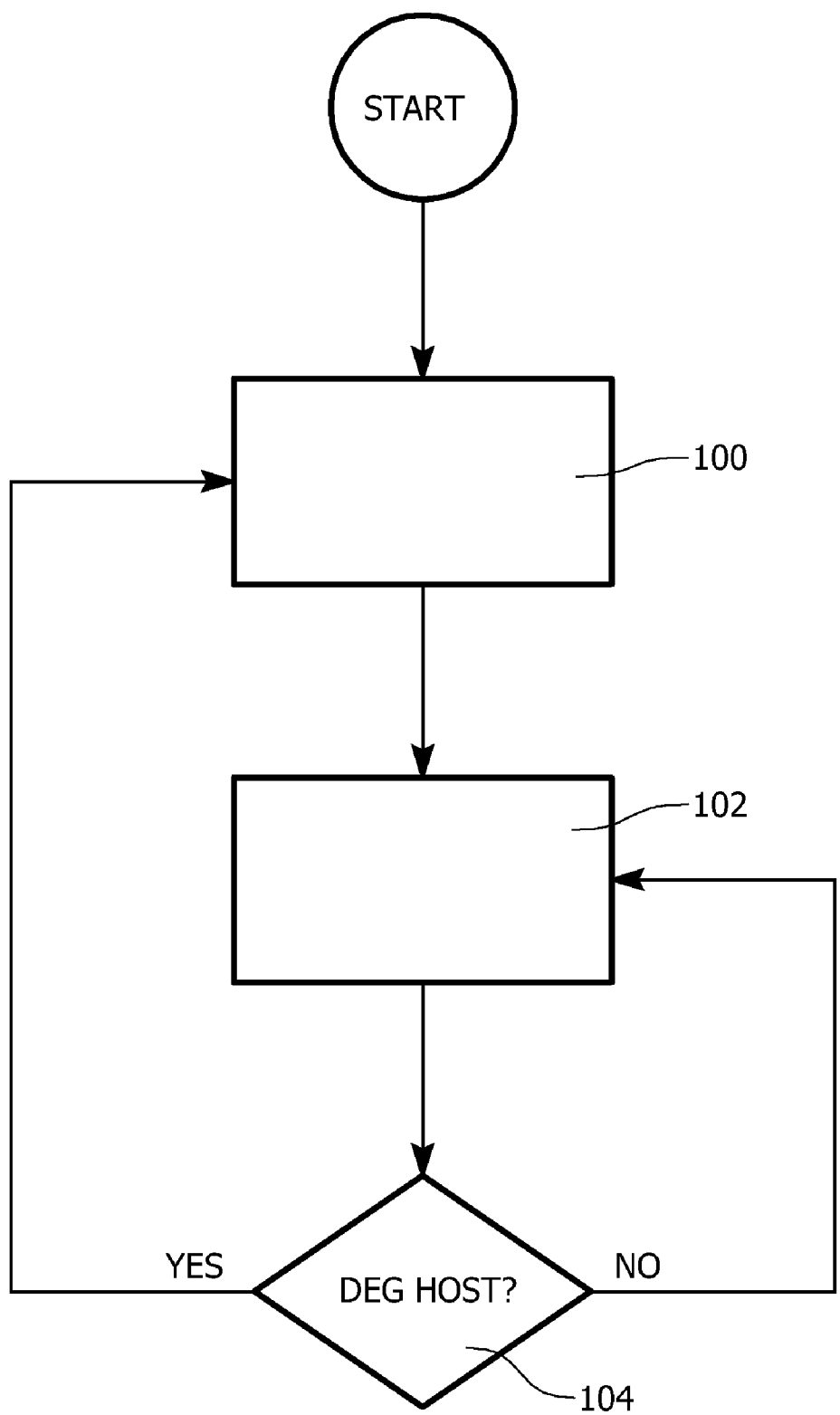
FIG. 4 is a schematic flow diagram illustrating the principal steps in a method according to an exemplary embodiment of the present invention.

Thus, in summary and referring to FIG. 4 of the drawings, a method according to the present invention comprises performing a deghosting scan 100 by acquiring an 'air' image at a relatively high detector dose, performing subsequent scans 102 in respect of respective subjects, determining 104 when a predetermined period of time has elapsed since the last deghosting scan was performed, and repeating the deghosting scan.

It should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa. The invention may be implemented by means of hardware comprising several distinct elements, and by means of a suitably programmed computer. In a device claim enumerating several means, several of these means may be embodied by one and the same item of hardware. The mere fact that certain measures are recited in mutually different dependent claims does not indicate that a combination of these measures cannot be used to advantage.

The invention claimed is:

1. A method for reducing differential ghosting in an X-ray image acquired in respect of a subject using an X-ray system comprising an X-ray source for irradiating said subject and an X-ray detector for receiving X-radiation that has passed through said subject and generating an electric signal representative of the intensity distribution thereof, said X-ray detector comprising a scintillator for receiving X-radiation incident thereon and converting said X-radiation into optical radiation, the method comprising acts of:

prior to acquiring the X-ray image, acquiring a deghost scan when no subject is present between said X-ray source and the X-ray detector by
causing said X-ray source to generate an X-radiation beam at a higher X-radiation dose than when the x-ray image is acquired, and
causing said detector to receive said X-radiation and generate an electric signal representative of homogeneous ghosting caused in said detector by said X-radiation incident thereon.

2. The method according to claim 1, wherein said deghost scan is performed only once daily.

3. The method according to claim 1, wherein said deghost scan is performed automatically when said X-ray system is switched on.

4. The method according to claim 1, wherein said deghost scan is performed at 40 mGy.

5. The method according to claim 1, the method comprising an act of repeating the acquiring of a deghost scan act after a predetermined period of time has elapsed from a previously acquired deghost scan.

6. A method for reducing differential ghosting in an X-ray image acquired in respect of a subject using an X-ray system comprising an X-ray source for irradiating the subject and an X-ray detector for receiving X-radiation, the X-ray detector comprising a scintillator for receiving X-radiation incident thereon and converting the X-radiation into optical radiation, the method comprising acts of:

prior to acquiring the X-ray image of the subject, producing a deghost scan when no subject is present between said X-ray source and the X-ray detector by generating an X-radiation beam without a subject present at a higher X-radiation dose than when the x-ray image of the subject is acquired, and receiving at a detector said X-radiation without the subject present and thereby, generating an electric signal representative of homogeneous ghosting image caused in said detector;

producing a scan when the subject is present; and acquiring the X-ray image of the subject with the X-ray detector, wherein the x-ray image of the subject includes the homogeneous ghosting image produced by the deghost scan.

7. The method according to claim 6, wherein the deghost scan is performed at 40 mGy.

8. The method according to claim 6, the method comprising an act of repeating the producing a subsequent deghost scan act after a predetermined period of time has elapsed from a prior deghost scan.

* * * * *